United States Patent
Nebolsin

(10) Patent No.: US 11,571,411 B2
(45) Date of Patent: Feb. 7, 2023

(54) USE OF A BISAMIDE DERIVATIVE OF MALONIC ACID FOR TREATING ALLERGIC AND OTHER DISEASES IN HUMANS AND ANIMALS

(71) Applicant: PHARMENTERPRISES ALLERGY LLC, Moscow (RU)

(72) Inventor: Vladimir Evgenievich Nebolsin, Pavlovskaya Sloboda (RU)

(73) Assignee: PHARMENTERPRISES ALLERGY LLC, Moscow (RU)

( * ) Notice: Subject to any disclaimer, the term of this patent is extended or adjusted under 35 U.S.C. 154(b) by 262 days.

(21) Appl. No.: 17/058,105

(22) PCT Filed: May 22, 2019

(86) PCT No.: PCT/RU2019/050066
§ 371 (c)(1),
(2) Date: Nov. 23, 2020

(87) PCT Pub. No.: WO2019/226082
PCT Pub. Date: Nov. 28, 2019

(65) Prior Publication Data
US 2021/0361624 A1    Nov. 25, 2021

(30) Foreign Application Priority Data
May 24, 2018 (RU) .......................... RU2018119193

(51) Int. Cl.
*A61K 31/4178* (2006.01)
*A61P 37/08* (2006.01)
*A61K 45/06* (2006.01)

(52) U.S. Cl.
CPC .......... *A61K 31/4178* (2013.01); *A61K 45/06* (2013.01); *A61P 37/08* (2018.01)

(58) Field of Classification Search
None
See application file for complete search history.

(56) References Cited

U.S. PATENT DOCUMENTS

2016/0031858 A1 * 2/2016 Nebolsin ............. C07D 277/28
548/204

* cited by examiner

*Primary Examiner* — Jeffrey S Lundgren
*Assistant Examiner* — Michael J Schmitt
(74) *Attorney, Agent, or Firm* — BCF LLP

(57) ABSTRACT

The invention relates to the therapy of diseases associated with the activity of histamine receptors, in particular for the treatment of allergic diseases, preferably the therapy of perennial and persistent allergic rhinitis, itch, as well as a number of other diseases associated with the activity of histamine receptor type 3 and/or 4, using compound N,N'-bis(2-(1H-imidazol-5-yl)ethyl)malonamide.

(I)

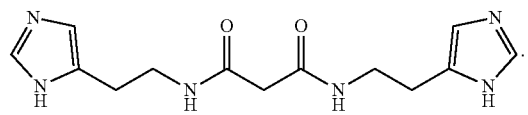

This compound, as well as pharmaceutically acceptable salts, hydrates, or solvates thereof, is an antagonist of histamine receptor type 3 and/or 4. The invention also relates to pharmaceutical compositions containing a therapeutically effective amount of Compound I.

4 Claims, No Drawings

USE OF A BISAMIDE DERIVATIVE OF MALONIC ACID FOR TREATING ALLERGIC AND OTHER DISEASES IN HUMANS AND ANIMALS

CROSS REFERENCE TO RELATED APPLICATIONS

This application is a national stage application under 35 U.S.C. § 371 of International Application No. PCT/RU2019/050066, filed internationally on May 22, 2019, which claims priority to Russian Application No. 2018119193, filed on May 24, 2018, the contents of which is hereby incorporated by reference.

FIELD OF THE INVENTION

The invention relates to chemistry of organic compounds, pharmacology and medicine and is directed to the treatment of diseases associated with the overactivation of histamine receptors, in particular the treatment of perennial and persistent allergic rhinitis, using a compound effective in inhibiting activity of histamine receptor type 3 (H3) and type 4 (H4) involved particularly in the processes of vasodilation, oedema, and inflammation in the nasal cavity, and pain symptoms.

BACKGROUND

Histamine receptors represent a class of G protein-coupled receptors which bind histamine as their primary endogenous ligand. Histamine receptors are involved in a number of physiological processes associated with development of various pathological conditions. In particular, histamine H1 or H2 receptor antagonists are widely used in the treatment of allergic and gastrointestinal disorders (Br J Pharmacol. 2009 May; 157(1):24-33).

Histamine receptor type 3 was first identified in 1983 in human brain and a number of laboratory animals (Nature 1983; 302(5911):832-837). The histamine receptor type 3 is expressed in the brain regions that are critical for cognition (cerebral cortex and hippocampus) and circadian rhythm regulation (hypothalamus) (Expert Opin. Investig. Drugs 2004; 13(10):1237-1248). Histamine is a highly potent H3 receptor agonist. H3 agonist-induced activation of H3 receptors in the brain regulates the release and synthesis of histamine and a number of other neurotransmitters that play a role in regulating attention, impulsivity and food intake. This is why H3 receptor antagonists are currently being studied in several therapeutic areas, including cognitive and sleep disorders (Expert Opin. Investig. Drugs 2007; 16(7): 967-985). Thus, H3 receptors of the central nervous system are an attractive drug target for both scientific research and pharmaceutical industry (Biochem. Pharmacol. 2007; 73(8): 1084-1096, Biochem. Pharmacol. 2006; 71(8):1103-1113). However, it should be noted that exposure to H3 receptors in the brain can cause a number of undesirable side effects, such as the development of depression, sleep disturbances, etc.

Later it was found that histamine third receptors were also expressed in peripheral tissues and localized on the epithelium and nerves in human nasal mucosa (Mol. Pharmacol. 1999; 55(6):1101-1107). This discovery made it possible to consider peripheral type 3 histamine receptors as a promising target for the treatment of certain allergic conditions and, in particular, allergic rhinitis. An allergic reaction in the nasal cavity initiates degranulation of mast cell and histamine release, which in turn acts on postsynaptic H1 receptors, causing extravasation with H1-mesions, vasodilation and mucus secretion. In addition, histamine causes vasodilation by activating presynaptic H3 receptors located on postganglionic sympathetic neurons, which leads to a decrease in norepinephrine release, increased vascular permeability, the development of edema and pain symptoms. In addition, the activation of H3 receptors located on nociceptive sensory nerves induces the release of substance P, which in turn causes rhinorrhea and nasal congestion (Am. Rev. Respir. Dis. 1991; 144:630-5; J. Pharmacol. Sci. 2008; 108:206-11).

While the expression of histamine receptor type 3 in peripheral tissues is limited to the epithelium and nerve endings of the nasal mucosa, histamine receptor type 4 is widely expressed on the surface of immune system cells (Br. J. Pharmacol. 2009 May; 157(1):24-33). The activation of histamine receptor type 4 modulates migration of eosinophils (Br. J. Pharmacol. 2004 May; 142(1):161-71; Cytometry A. 2008; 73:299-304) and selective recruitment of mast cells (J Invest Dermatol. 2004 July; 123(1):116-23; J. Pharmacol. Exp. Ther. 2004; 309:404-413), leading to amplification of histamine-mediated immune responses and eventually to chronic inflammation.

On various animal models, as well as in studies on healthy volunteers, it was shown that the simultaneous blockade of peripheral H3 and H4 receptors could have a positive effect for the treatment of allergic rhinitis, as well as other inflammatory diseases. It was shown that intranasal administration of a type 4 histamine receptor antagonist caused a significant decrease in the nasal symptoms of the disease and a decrease in the level of interleukin-4 (Int Immunopharmacol. 2009 June; 9(6):734-8). Similarly, intranasal administration of R-alpha-methylhistamine, an H3 receptor agonist, induced nasal blockage in humans, which was reduced by topical administration of the H3 receptor antagonist thioperamide (Br. J. Pharmacol. 2005 March; 144(6):867-74). In vitro studies of tissue samples from pigs and humans shown that R-alpha-methylhistamine induced vasodilation by reducing the release of the vasoconstrictor noradrenaline from nasal sympathetic nerve endings (Eur. J. Pharmacol. 2004; 484: 83-9; Eur. J. Pharmacol. 2002; 452:339-45). It is important to note that in addition to suppressing nasal symptoms of allergic rhinitis, peripheral antagonists of histamine receptor type 4 can effectively suppress histamine-induced itch (J. Pharmacol. Exp. Ther. 2014 July; 350(1):181-7).

Several antagonists of histamine receptor types 3 and 4 (H3 receptors and H4 receptors) were studied in clinical trials for the treatment of allergic rhinitis. In Phase 2 clinical trials, all three H3 antagonists showed to be effective in controlling allergic rhinitis symptoms. However, since all three drugs had the ability to cross the blood-brain barrier and block H3 receptors in the central nervous system, all data on drug candidates were, to greater or lesser extent, associated with the development of side effects. In addition, the selective H4 receptor antagonist JNJ-7777120 was effective in an animal model of allergic rhinitis.

To date, Thioperamide is the only a dual H3 and H4 receptor antagonist that has been tested in clinical trials. The antagonist was shown to cross the blood-brain barrier and lead to the development of central nervous system side effects. Thus, the known H3 receptor antagonists either fail to demonstrate a desired selectivity for H3 and H4 receptors, or they penetrate the blood-brain barrier and are not suitable for the clinical development of drugs for the treatment of allergic rhinitis.

Thus, to date, there are no known drugs that act as an antagonist of histamine receptor types 3 and 4, which would be used in the treatment of allergic diseases in humans. Therefore, there remains a need to create and introduce into the clinic new effective drugs based on an antagonists of histamine receptor type 3.

The invention relates to use of a chemical compound effective in suppressing the activity of histamine receptors in the treatment of allergic diseases (such as perennial and persistent allergic rhinitis), as well as other diseases associated with the overstimulation of histamine receptor types 3 and 4.

SUMMARY OF THE INVENTION

The objective of the present invention is to develop a new drug, which is an antagonist of histamine receptor types 3 and 4 (a histamine H3/H4 receptor antagonist) and is effective for the treatment of itch and allergic diseases, preferably for the treatment of perennial and persistent allergic rhinitis and other diseases associated with the activity of histamine receptor types 3 and 4.

The technical result of the invention is the development and preparation of an effective antagonist of histamine receptor types 3 and 4 characterized by a high activity and pharmacokinetic characteristics suitable for use, in particular, for oral and intranasal administration in the treatment of itch and allergic diseases, such as perennial and persistent allergic rhinitis.

The specified technical result is achieved by providing a histamine H3/H4 receptor antagonist, which is the compound N,N'-bis(2-(1H-imidazol-5-yl)ethyl)malonamide (or N,N'-bis[2-(1H-imidazol-4-yl)ethyl]propane diamide, Compound I)

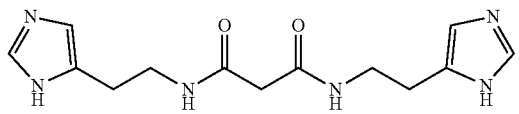 [SMILES: O=C(CC(=O)NCCc1cnc[nH]1)NCCc1cnc[nH]1]

or a pharmaceutically acceptable salt, hydrate or solvate thereof.

An object of the present invention is use of the antagonist as described above for prevention and/or treatment of a disorder associated with the activity of histamine receptor types 3 and 4, including itch and allergic disorders, in particular perennial or persistent allergic rhinitis and itch.

The technical result is also achieved using N,N'-bis(2-(1H-imidazol-5-yl)ethyl)malonamide or a pharmaceutically acceptable salt, hydrate, or solvate thereof for preparing a pharmaceutical composition for the prevention and/or treatment of a disorder associated with the activity of histamine receptor types 3 and 4, the pharmaceutical composition comprising a therapeutically effective amount of the antagonist as described above and at least one pharmaceutically acceptable carrier. The disorder associated with the activity of histamine receptor types 3 and 4 includes an allergic disorder, in particular, perennial or persistent allergic rhinitis.

The pharmaceutical composition may further comprise one or more other therapeutic agents, wherein the other additional therapeutic agent comprises those selected from an antihistamine, sodium cromoglycate, an intranasal glucocorticoid, ipratropium bromide, a vasoconstrictor, an antibiotic, a non-steroidal anti-inflammatory agent, or an analgesic agent.

The specified technical result is also achieved using Compound I or a pharmaceutically acceptable salt, hydrate, or solvate thereof in the manufacture of a medicament for the prevention and/or treatment of a disorder associated with the overstimulation of histamine receptor types 3 and 4.

In addition, the invention provides pharmaceutical compositions for the prevention and/or treatment of a disorder associated with the activity of histamine receptor types 3 and 4, characterized in that the compositions comprise an effective amount of the compound according to the invention and at least one pharmaceutically acceptable additive. In some embodiments, the additive is a pharmaceutically acceptable carrier and/or excipient.

The invention also includes a method for preventing and/or treating a disorder associated with the overactivation of histamine receptor types 3 and 4 in an organism, comprising administering Compound I according to the invention to said organism. The disorder associated with the activity of histamine receptor types 3 and 4 is itch or an allergic disease, especially a disease of the lungs and respiratory tract. In some non-limiting embodiments, the disease is perennial and/or persistent allergic rhinitis. In particular embodiments of the invention, the organism is a human or animal organism.

The invention also relates to a method for preventing and/or treating a disorder associated with the activity of histamine receptor types 3 and 4 in a subject in need of such treatment, comprising administering a therapeutically effective amount of Compound I to said subject.

The invention also relates to a histamine H3/H4 receptor antagonist, which is Compound 1:

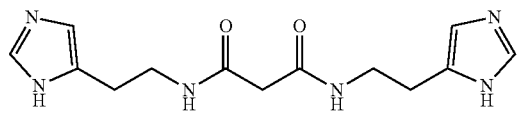 [SMILES: O=C(CC(=O)NCCc1cnc[nH]1)NCCc1cnc[nH]1]

or a pharmaceutically acceptable salt, hydrate, or solvate thereof.

The invention also relates to use of histamine receptor types 3 and 4, which is Compound 1, or a pharmaceutically acceptable salt, hydrate or solvate thereof according to the invention for the prevention and/or treatment of a disorder associated with the activity of histamine receptor types 3 and 4, including itch, allergic disorders, in particular perennial or persistent allergic rhinitis.

The invention also relates to a method for preventing and/or treating perennial or persistent allergic rhinitis in a subject in need of such treatment, comprising administering a therapeutically effective amount of Compound I to said subject.

The invention also relates to use of Compound I for the manufacture of a medicament.

Further, the present invention relates to a combination comprising Compound I with one or more other additional therapeutic agents.

The invention also relates to a method for decreasing the overactivation of histamine receptor types 3 and 4, comprising administering an effective amount of Compound 1 alone or in combination with pharmaceutically acceptable fillers.

In addition, the invention relates to a method of treating a mammal, including a human, against a disorder that can be treated with antagonists of one or both of histamine receptors of type 3 (H3) and type 4 (H4), including simultaneous, separate or sequential administration of an effective amount of Compound alone or in combination with pharmaceutically acceptable fillers to the mammal.

The compound N,N'-bis(2-(1H-imidazol-5-yl)ethyl)malonamide compound is known and described in patent application RU 2013/116822.

DETAILED DESCRIPTION OF THE INVENTION

The process for preparing Compound 1 is described in patent application RU 2013/116822. The patent application describes bisamide derivatives of dicarboxylic acids with the ability to complex or chelate metal ions and their use as an agent for the prevention and/or treatment of viral hepatitis, HIV infection, oncological, neurodegenerative, cardiovascular, and inflammatory diseases, diabetes, gerontological diseases, diseases caused by microbial toxins, as well as alcoholism, alcoholic liver cirrhosis, anemia, *Porphyria tarda*, and poisoning with transition metal salts.

The inventor of the present invention has surprisingly found that Compound I is an antagonist of histamine receptor types 3 and 4. The use of Compound I is perspective for the treatment of itch and allergic diseases, in particular, for the treatment of perennial and persistent allergic rhinitis.

Thus, Compound I can be used in the treatment of itch and allergic diseases, such as perennial and persistent allergic rhinitis.

Terms and Definitions

The term "Compound I" refers to N,N'-bis(2-(1H-imidazol-5-yl)ethyl)malonamide (N,N'-bis[2-(1H-imidazol-4-yl)ethyl]propanediamide), also represented by the structural formula:

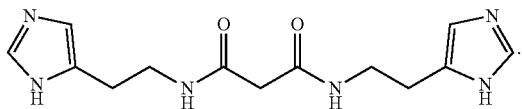 [SMILES: O=C(CC(=O)NCCc1cnc[nH]1)NCCc1cnc[nH]1]

The term "C" when used with reference to the temperature means centigrade or Celsius temperature scale.

The term "$IC_{50}$" means the concentration of a test compound, at which half-maximal inhibition of the enzyme is achieved.

The term "pharmaceutically acceptable salts" or "salts" includes salts of active compounds which are prepared with relatively nontoxic acids. Examples of pharmaceutically acceptable nontoxic salts include salts formed with inorganic acids such as hydrochloric, hydrobromic, phosphoric, sulfuric and perchloric acids, or organic acids such as acetic, oxalic, maleic, tartaric, succinic, citric or malonic acids, or prepared by others methods used in the field, for example, through ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentane propionate, digluconate, dodecylsulfate, ethanesulfonate, formate, fumarate, glucoheptonate, glycerophosphate, gluconate, hemisulfate, heptanate, hexanate, hydroiodide, 2-hydroxyethanesulfonate, lactobionate, lactate, laurate, lauryl sulfate, malate, maleate, malonate, methanesulfonate (mesylate), 2-naphthalenesulfonate, nicotinate, nitrate, oleate, oxalate, palmitate, pamoate, pectinate, persulfate, 3-phenylpropionate, phosphate, picrate, pivalate, propionate, hemifumarate, stearate, succinate, sulfate, tartrate, thiocyanate, p-toluenesulfonate (tosylate), undecanate, valerate and the like.

The term "solvate" is used to describe a molecular complex comprising a compound according to the invention and one or more molecules of a pharmaceutically acceptable solvent, such as ethanol. The term "hydrate" is used when the solvent is water.

The term "additive" means any pharmaceutically acceptable inorganic or organic substance comprised in a medicament or used in the process for producing or manufacturing a medicament, to ensure necessary physicochemical properties.

The terms "treatment" and "therapy" encompass the treatment of pathological conditions in mammals, preferably in humans, and include: a) reduction, b) blockage (suspension) of disease progression, c) alleviation of disease severity, i.e. induction of disease regression, d) reversal of a disease or condition to which the term refers, or one or more symptoms of the disease or condition.

The term "prophylaxis" or "prevention" encompasses the elimination of risk factors, as well as prophylactic treatment of a subclinical disease in mammals, preferably in humans, aimed at reducing the risk of its clinical presentation. Patients for prophylactic therapy are selected based on factors that are known to entail an increased risk of clinical disease compared with the general population. Preventive therapy includes a) primary prevention and b) secondary prevention. Primary prevention is defined as prophylactic treatment of patients having a disease that has not yet become clinically evident. Secondary prevention is the prevention of the recurrence of the same or a similar clinical condition of a disease.

Compound I is promising for the treatment of diseases associated with the activity and, in particular, overstimulation of histamine receptor types 3 and 4, in particular, for the treatment of both systemic and local allergic diseases, including those associated with various diseases or caused by long-term use of certain medicaments.

Method for Therapeutic Use of Compounds

The object of the invention also includes the administration of a therapeutically effective amount of a compound according to the invention to a subject in need of appropriate treatment. The therapeutically effective amount means the amount of a compound administered or delivered to a patient that most likely ensures a desired patient response to the treatment (prophylaxis). The exact amount required can vary from subject to subject depending on the age, body weight and general condition of the patient, disease severity, route of administration, selected regimen of combined treatment with other drugs, and the like.

Compound I or a pharmaceutical composition comprising Compound I can be administered to a patient in any reasonable amount (preferably, the daily dose of the active ingredient is up to 0.5 g per patient per day, most preferably, the daily dose is from 5 to 50 mg/day) and by any route of administration (preferably oral administration) effective for treating or preventing a disease.

After mixing the drug with a particular suitable pharmaceutically acceptable carrier at a desired dosage, compositions according to the invention can be administered to humans or other animals orally, parenterally, topically, and the like.

The administration can be performed once or several times per a day, week (or any other time interval), or from time to time. In addition, a compound can be administered to a patient daily over a certain period of days (e.g., from 2 to 10 days), followed by a period without administration (e.g., from 1 to 30 days).

When compound (I) is used as part of a combination therapy regimen, the dose of each component of the combination therapy is administered over a desired treatment period. The compounds, which are part of the combination therapy, can be administered to patient's body both simultaneously as a dosage comprising all components and as individual dosages of the components.

Pharmaceutical Compositions

The invention also relates to pharmaceutical compositions comprising Compound I (or a prodrug or other pharmaceutically acceptable derivative, in particular a salt, hydrate or solvate) and one or more pharmaceutically acceptable carriers, adjuvants, diluents and/or excipients, which can be administered to a patient together with Compound I and which do not affect the pharmacological activity of the compound and are nontoxic when administered in doses sufficient to deliver a therapeutic amount of Compound I.

Pharmaceutical compositions according to the present invention comprise Compound I together with pharmaceutically acceptable carriers that may include any solvents, diluents, dispersions or suspensions, surfactants, isotonic agents, thickeners and emulsifiers, preservatives, binders, glidants etc., which are suitable for a particular dosage form. Materials that can serve as pharmaceutically acceptable carriers include, but are not limited to, mono- and oligosaccharides and derivatives thereof; gelatin; talc; excipients such as cocoa butter and suppository wax; oils such as peanut, cottonseed, safrole, sesame, olive, corn, and soybean oils; glycols such as propylene glycol; esters such as ethyl oleate and ethyl laurate; agar; buffering agents such as magnesium hydroxide and aluminum hydroxide; alginic acid; pyrogen-free water; isotonic solution, Ringer's solution; ethyl alcohol and phosphate buffer solutions. The composition may also comprise other non-toxic compatible lubricants such as sodium lauryl sulfate and magnesium stearate, as well as colorants, film formers, sweeteners, flavors, preservatives, and antioxidants.

The invention also relates to medicaments, which means pharmaceutical formulations, the composition of which is optimized for a specific route of administration to the body in a therapeutically effective dose, for example, for administration to the body orally, topically, by inhalation, for example in the form of an inhalation spray, or intravascularly, intranasally, subcutaneously, intramuscularly, or by infusion, in recommended dosages.

Medicaments according to the present invention may comprise formulations prepared by liposome methods, microencapsulation methods, methods for producing nanoform preparations or other methods known in the pharmaceutical industry.

When preparing a medicament, for example in the form of a tablet, the active principle is mixed with one or more pharmaceutically acceptable excipients such as gelatin, starch, lactose, magnesium stearate, talc, silica, gum arabic, mannitol, microcrystalline cellulose, hypromellose or the like.

Tablets may be coated with sucrose, a cellulose derivative, or other suitable coating materials. Tablets can be produced by various methods, such as direct compression, dry or wet granulation, or hot fusion.

A medicament in the form of a gelatin capsule can be prepared by mixing Compound I with other components and filling the resulting mixture into soft or hard capsules.

For parenteral administration, aqueous suspensions, isotonic saline solutions, or sterile injectable solutions are used that contain pharmacologically compatible agents, for example propylene glycol or butylene glycol.

Examples of Pharmaceutical Compositions

Compound I can be used for the prevention and/or treatment of diseases of humans or animals in the form of the following formulations ("Substance" means the active ingredient in the form of Compound I or a pharmaceutically acceptable salt, hydrate or solvate thereof):

Tablet I, Mg/Tablet
Substance, 2.0
Microcrystalline Cellulose, 73.2;
Sodium Carboxymethyl Starch, 4.0;
Magnesium Stearate, 0.8;
Tablet II, Mg/Tablet
Substance, 10.0
Microcrystalline Cellulose, 366.0;
Sodium Carboxymethyl Starch, 20.0;
Magnesium Stearate, 4.0;
Tablet III, Mg/Tablet
Substance, 20.0
Microcrystalline Cellulose, 732.0;
Sodium Carboxymethyl Starch, 40.0;
Magnesium Stearate, 8.0;
Tablet IV, Mg/Tablet
Substance, 50
Lactose Ph. Eur, 223.75;
Sodium Croscarmellose, 6.0;
Corn Starch, 15;
Polyvinylpyrrolidone (5% w/v paste), 2.25;
Magnesium Stearate, 3.0;
Tablet V, Mg/Tablet
Substance, 200
Lactose Ph. Eur, 182.75;
Sodium Croscarmellose, 12.0;
Corn Starch (5% w/v paste), 2.25;
Magnesium Stearate, 3.0;
Capsule, Mg/Capsule
Substance, 10
Lactose Ph. Eur, 488.5;
Magnesia, 1.5;
Formulation I for Injections (50 mg/ml)
Substance, 5.0% w/v
1M Sodium Hydroxide, 15.0% w/v
1M HCl up to pH=7.6
Polyethylene Glycol 400, 4.5% w/v
Water for Injection, up to 100%
Ointment (mL)
Substance, 40 mL
Ethanol, 300 μL
Water, 300 μL
1-Dodecylazacycloheptanone, 50 μL
Propylene glycol, up to 1 mL
Intranasal Formulation I (mg/mL)
Substance, 10.0
Sodium Citrate Dihydrate, 3.823
Citric Acid Monohydrate, 0.609
Glycerin, 25.0
Dextrose, 5.5
Benzyl Alcohol 2.5
Water, up to 100 g %

Intranasal Formulation II (mg/ml)
Substance, 10.0
Sodium Citrate Dihydrate, 3.823
Citric Acid Monohydrate, 0.609
Glycerin, 25.0
Dextrose, 5.5
Water, up to 100 g %
Intranasal Formulation III (mg/ml)
Substance, 10.0
Sodium Dihydrogen Phosphate Dihydrate, 3.38
Disodium Hydrogen Phosphate Dihydrate, 2.08
Glycerin, 25.0
Dextrose, 5.5
Benzyl Alcohol 2.5
Water, up to 100 g %
Intranasal Formulation IV (mg/ml)
Substance, 10.0
Sodium Dihydrogen Phosphate Dihydrate, 3.38
Disodium Hydrogen Phosphate Dihydrate, 2.08
Glycerin, 25.0
Dextrose, 5.5
Benzyl Alcohol 2.5
Water, up to 100 g %

The formulations may be prepared in accordance with standard techniques. Tablets (I)-(V) may be enteric coated using, for example, cellulose acetate phthalate.

Use of Compound I in Combination Therapy

Despite the fact that Compound I according to the invention can be administered as an individual active ingredient, it can also be used in combination with one or more other active ingredients, in particular, the other active ingredient can be an antihistamine, sodium cromoglycate, intranasal glucocorticoid, ipratropium bromide, vasoconstrictor, antibiotic, non-steroidal anti-inflammatory drug (NSAID) or another anti-inflammatory agent, etc. When administered in combination, therapeutic agents can be formulated in different dosage forms which are administered simultaneously or sequentially at different times, or the therapeutic agents can be combined into a single dosage form.

The phrase "combination therapy" used in relation to the compounds according to the invention in combination with other pharmaceutical agents means simultaneous or sequential administration of all agents, which will, in one way or another way, provide a beneficial effect of the combination of drugs. Co-administration includes, in particular, co-delivery, for example in one tablet, capsule, injection or other form, having a fixed ratio of active substances, as well as simultaneous delivery in several, separate dosage forms for each compound, respectively.

Thus, Compound I can be administered in combination with additional therapies known to those skilled in the prevention and treatment of relevant diseases, including the use of antibacterial and anti-inflammatory drugs, drugs to suppress symptoms or side effects of one of the drugs.

If the dosage form is a fixed dose, such a combination comprises a compound according to the invention within an acceptable dose range. Compound I according to the invention can also be administered to a patient sequentially with other agents, when a combination of these drugs is not possible. The invention is not limited to sequential administration; Compound I can be administered to a patient together, before or after administration of another drug.

EXAMPLES

Preparation of Compound I

The preparation of Compound I is described in patent application RU 2013/116822. The same application describes the ability of Compound I to complex or chelate metal ions.

Characterization of the Biological Activity of Compounds According to the Invention The biological activity of Compound I has been studied in various in vitro and in vivo experiments. In particular, the studies of the activity of Compound I in various in vitro and in vivo models have shown that Compound I has an inhibitory effect in the model of ovalbumin-induced allergic rhinitis in guinea pigs. This biological activity of Compound I cannot be predicted or explained based on the previously known ability of Compound I to chelate metal ions.

From the studies of the biological activity of Compound I in vitro it has been found that Compound I is an antagonist of histamine receptor type 3. The activity of Compound I in models of allergic rhinitis seems to relate to its action on the above receptor.

Example 1. Study of the Effect of Compound I on the Activity of Histamine Receptor Type 3

Compound I was dissolved in DMSO to a concentration of 100 mM; then the stock solution was serially diluted with DMSO. The maximum starting concentration of the substance was 100 µM. The effect was determined at 8 concentrations of the test compound; each concentration was tested in duplicate. The cells used in the experiment were CHO cells expressing human histamine receptor type 3, which were incubated with Compound I after preincubation with histamine. The activity of the receptors was determined by the intracellular concentration of cAMP using fluorescence spectroscopy (Lim, H. D. et al. (2005) J. Pharmacol. Exp. Ther., 314:1310-1321).

In the study, it was found that Compound I was an antagonist of histamine receptor type 3 with $IC_{50}=20$ µM.

Example 2. Study of the Effect of Compound I on the Binding of a Radiolabeled Ligand to Histamine Receptor Type 3

Compound I was dissolved in DMSO to a concentration of 300 mM; then the stock solution was serially diluted with DMSO. The maximum starting concentration of the substance was 300 µM. The effect was determined at 10 concentrations of the test compound; each concentration was tested in duplicate. The cells used in the experiment were CHO cells expressing human histamine receptor type 3, which were incubated with Compound I after preincubation with [3H]Nα-methylhistamine (1 nM). The activity of Compound I was determined by the concentration of the displaced radioactively labeled ligand (Lovenberg, T. W. et al. (1999), Mol. Pharmacol., 55:1101-1107).

In the study, it was found that Compound I bound to histamine receptor type 3 with a Ki value of 2.7 µM.

Example 3. Study of the Effect of Compound I on the Binding of a Radiolabeled Ligand to Histamine Receptor Type 4

Compound I was dissolved in DMSO to a concentration of 300 mM; then the stock solution was serially diluted with DMSO. The maximum starting concentration of the substance was 300 µM. The effect was determined at 10 different concentrations of the test compound; each concentration was tested in duplicate. The cells used in the experiment were HEK-293 cells expressing human histamine receptor type 4, which were incubated with Compound I after preincubation with [3H] histamine (10 nM). The activity of Compound I was determined by the concentration of the displaced radioactively labeled ligand (Liu, C. et al. (2001), J. Pharmacol. Exp. Ther., 299:121-130).

In the study, it was found that Compound I bound to histamine receptor type 4 with a Ki value of 16 μM.

Example 4. Study of Activity of Compound I on an Ovalbumin-Induced Allergic Rhinitis Model in Guinea Pigs The allergic rhinitis model was performed according to the standard procedure [Thakare V. N., Osama M. M., Naik S. R. Therapeutic potential of curcumin in experimentally induced allergic rhinitis in guinea pigs. Int Immunopharmacol. 2013. V.17(1). P.18-25]. Guinea pigs (250-300 g) were immunized with 4× (on days 0, 7, 14 and 21) intraperitoneal administration of a mixture of ovalbumin (100 μg/pig) and aluminum hydroxide (5 mg/pig), diluted and suspended in saline. On day 28 of the study, an ovalbumin solution (60 mg/ml) was injected intranasally to the animals, 20 μl into each nostril. On day 35, after shaving the skin on the back, the animals were intradermally injected with an ovalbumin solution (200 μg/ml, 25 μl). The presence of sensitization was confirmed by swelling and redness at the injection site. On day 42 of the study, an ovalbumin solution (60 mg/ml, 20 μl/nostril) was administered intranasally. A group of sham-immunized animals was formed in order to control the formation of allergic inflammation: the pigs received an aluminum hydroxide solution (5 mg/pig) on days 0, 7, 14 and 21, a saline solution on days 28 and 35, and an ovalbumin solution (60 mg/ml, 20 μl/nostril) on day 42. Table 1 presents data on clinical manifestations of pathology and the number of eosinophils in the lavage fluid in guinea pigs on the allergic rhinitis experimental model after oral administration (M±m, n=10)

number of sneezes and nose scratchings in the experimental animals, which is indicative of the correctness of the implemented allergic rhinitis model. Intragastric administration of Compound I reduced the number of clinical manifestations of rhinitis and the influx of eosinophils into the nasal cavity (Table 1). The results suggest that Compound I, when orally administered, has a pronounced therapeutic effect in allergic rhinitis.

Example 5. Study of the Activity of a 1% Solution of Compound I after Nasal Administration to Guinea Pigs in the Allergic Rhinitis Model The allergic rhinitis model was performed according to the standard procedure [Thakare V. N., Osama M. M., Naik S. R. Therapeutic potential of curcumin in experimentally induced allergic rhinitis in guinea pigs. Int Immunopharmacol. 2013. V.17(1). P.18-25]. Guinea pigs (250-300 g) were immunized with 4× (on days 0, 7, 14 and 21) intraperitoneal administration of a mixture of ovalbumin (100 μg/pig) and aluminum hydroxide (5 mg/pig), diluted and suspended in saline. On day 28 of the study, an ovalbumin solution (60 mg/ml) was injected intranasally to the animals, 20 μl into each nostril. On day 35, after shaving the skin on the back, the animals were injected intradermally with an ovalbumin solution (200 μg/ml, 25 μl). The presence of sensitization was confirmed by swelling and redness at the injection site. On day 42 of the study, an ovalbumin solution (60 mg/ml, 20 μl/nostril) was administered intranasally. A group of sham-immunized animals was formed in order to control the formation of allergic inflammation: the pigs received an aluminum hydroxide solution (5 mg/pig) on days 0, 7, 14 and 21, a saline solution on days 28 and 35, and an ovalbumin solution (60 mg/ml, 20 μl/nostril) on day 42.

A 1% solution of Compound I was administered to the animals intranasally once 1 hour or 3 hours before intranasal

TABLE 1

| Group | Dose, mg/kg | Number of sneezes | Number of nose scratchings | Number of eosinophils per 1 μL of lavage fluid |
|---|---|---|---|---|
| Intact | — | 1.0 ± 0.4 | 5.3 ± 1.1 | 87.4 ± 14.0 |
| Sham-immunization | — | 4.1 ± 0.9* | 10.5 ± 1.2* | 601.6 ± 52.0* |
| Control | — | 20.2 ± 1.8*# | 29.6 ± 4.2*# | 1985.0 ± 292.0*# |
| Compound I | 0.014 | 11.6 ± 1.4*#& | 16.1 ± 2*#& | 1300.5 ± 93.8*#& |
|  | 0.042 | 10.5 ± 1.2*#& | 16.2 ± 2.7*& | 1219.6 ± 159.4*#& |
|  | 0.14 | 8.3 ± 0.9*#& | 13.3 ± 1.3*& | 1141.5 ± 128.5*#& |
|  | 0.42 | 5.2 ± 0.6*& | 16.2 ± 2.0*#& | 1069.0 ± 139.4*#& |
|  | 1.4 | 6.9 ± 0.8*#& | 14.4 ± 3.3*& | 984.1 ± 111.0*#& |

Note:
*difference from the intact group by Student's t-test (p < 0.05)
difference from the sham-immunization group by Student's t-test (p < 0.05)
&difference from the control group by Student's t-test (p < 0.05)

Compound I was administered to animals intragastrically 48, and 1 hour before intranasal administration of ovalbumin. Clinical manifestations of rhinitis were assessed within 2 hours after the last administration of ovalbumin: the numbers of sneezes and nose scratchings were counted. In addition, eosinophils were counted in the nasal lavage fluid.

The clinical manifestations of allergic rhinitis occurring within 2 hours after the last intranasal administration of ovalbumin to animals showed a marked increase in the administration of ovalbumin in a volume of 10 μl/nostril. Clinical manifestations of rhinitis were assessed within 2 hours after the last administration of ovalbumin: the numbers of sneezes and nose scratchings were counted. In addition, eosinophils were counted in the nasal lavage fluid.

Table 2 shows clinical manifestations of pathology and the number of eosinophils in the lavage fluid of guinea pigs on the experimental model of allergic rhinitis in nasal administration of Compound I (M±m, n=10)

TABLE 2

| Group | Administration mode of Compound I | Number of sneezes | Number of nose scratchings | Number of eosinophils per 1 μL of lavage fluid |
|---|---|---|---|---|
| Intact | | 3.9 ± 1.0 | 5.6 ± 1.3 | 198.8 ± 59.9 |
| Sham-immunization | | 7.4 ± 0.8* | 22.5 ± 4.6* | 497.1 ± 112.8* |
| Control | | 16.3 ± 1.4*# | 40.8 ± 3.5*# | 2700.4 ± 539.0*# |
| Compound I (1% solution) | Once, intranasally, 1 hour before the last administration of ovalbumin | 3.1 ± 1.2#& | 14.5 ± 4.4& | 1416.9 ± 126.8*#& |
| Control | | 17.2 ± 1.2*# | 37.2 ± 3.3*# | 2560.5 ± 306.6* |
| Compound I (1% solution) | Once, intranasally, 3 hours before the last administration of ovalbumin | 3.9 ± 1.5& | 10.7 ± 2.1#& | 1490.1 ± 241.0*#& |

Note:
*difference from the intact group by Student's t-test (p < 0.05)
difference from the sham-immunization group by Student's t-test (p < 0.05)
&difference from the control group by Student's t-test (p < 0.05)

The clinical manifestations of allergic rhinitis, which occurred within 2 hours after the last intranasal administration of ovalbumin to animals, showed a marked increase in the number of sneezes and nose scratchings in the experimental animals, which is indicative of the correctness of the implemented allergic rhinitis model. Intranasal administration of the 1% solution of Compound I reduced the number of clinical manifestations of rhinitis and the influx of eosinophils into the nasal cavity (Table 2). The therapeutic effect was equally manifested in both modes of administration of the 1% solution of Compound I: in a single administration 1 hour before the last intranasal administration of ovalbumin and in a single administration 3 hours before the last intranasal administration of ovalbumin.

The results suggest that Compound I has a pronounced therapeutic effect in allergic rhinitis. The duration of the therapeutic effect is at least 3 hours.

Example 6. Study of the Activity of a 1% Solution of Compound I after Nasal Administration in a Histamine-Induced Nasal Congestion Model in Guinea Pigs A histamine-induced nasal congestion model in guinea pigs was performed according to the standard procedure [Slack R J1, Russell L J, Hall D A, Luttmann M A, Ford A J, Saunders K A, Hodgson S T, Connor H E, Browning C, Clark K L. Pharmacological characterization of GSK1004723, a novel, long-acting antagonist at histamine H(1) and H(3) receptors//Br J Pharmacol. 2011. V.164(6). P.1627-1641]. Guinea pigs were anesthetized, the trachea was isolated, and a cannula was inserted through it into the nasopharynx. The cannula was connected to a blood pressure sensor and artificial respirator (Ugo Basile). A 0.2% solution of histamine was inhaled for 3 minutes. The resistance to air flow in the nasal passages was assessed within 15 minutes after the end of inhalation of the histamine solution. Compound I was administered to guinea pigs once intranasally in the form of a 1% solution (10 μl/nostril) 1 hour and 4 hours before the inhalation of histamine. The area under the curve (AUC) that characterizes the resistance to air flow in the nasal passages at time points of 0-15 minutes was used as an integral indicator for objective assessment.

Table 3 shows the results of the study of the resistance to air flow in the nasal passages in guinea pigs, using an experimental model of histamine-induced nasal congestion in nasal administration, see $H_2O×c$, AUC (M±m).

TABLE 3

| Groups | Administration mode | Number of animals per group | Resistance in nasal passages, AUC |
|---|---|---|---|
| Intact | | 30 | 164.47 ± 13.87 |
| Control | Once, intranasally, | 30 | 467.94 ± 38.4* |
| Compound I (1% solution) | 1 hour before histamine inhalation | 30 | 317.95 ± 24.49*& |
| Intact | | 20 | 155.74 ± 23.58 |
| Control | Once, intranasally, | 20 | 479.75 ± 46.28* |
| Compound I (1% solution) | 3 hours before histamine inhalation | 20 | 281.75 ± 52.44*& |

Note:
*difference from the intact group by Student's t-test (p < 0.05)
&difference from the control group by Student's t-test (p < 0.05)

A single intranasal administration of the 1% solution of Compound I to guinea pigs in the histamine-induced nasal congestion model significantly reduced the resistance to air flow in the nasal passages (Table 3). The therapeutic effect was manifested in both modes of administration of the 1% solution of Compound I: in administration of 1 hour before inhalation of histamine and in administration of 4 hours before inhalation of histamine.

The results suggest that the 1% solution of Compound I has a pronounced therapeutic effect in the histamine-induced nasal congestion model in guinea pigs. The duration of the therapeutic effect is at least 4 hours.

Example 7. Study of the Activity of a 1% Solution of Compound I in Nasal Administration on a Histamine-Induced Nasal Congestion Model in Dogs A histamine-induced nasal congestion model in dogs was performed according to the standard procedure [Tiniakov R. L., Tiniakova O. P., McLeod R. L., Hey J. A., Yeates D. B. Canine model of nasal congestion and allergic rhinitis//J Appl Physiol. 2003. V.94(5). P.1821-1828]. Beagle dogs were injected to the nasal cavity with a 5% histamine solution in a volume of 250 μl/nostril. The volume of the nasal cavity of the right and left nostrils was measured using a rhinometer before and 5, 10, 15, 20, 30, 40, 50 and 60 minutes after administration of histamine. Five experiments were carried out in which Compound I was administered intranasally once in the form of a 1% solution in a volume of 50 µl at different time periods: 1) 5 minutes after the administration of histamine; 2) right before administration of histamine; 3) 3 hours before administration of histamine; 4) hours before administration of histamine; and 5) 8 hours before administration of histamine.

The results of the study showed that the inhalation of the 5% histamine solution in dogs reduces the volume of the nasal cavity of the animals' nostrils. A single intranasal administration of the 1% solution of Compound I provided a significant dose-dependent increase in the reduced volume of the nostril nasal cavity of dogs. In table 4, the volume of the nasal cavity of the right and left nostrils in dogs was measured on the experimental model of histamine-induced nasal congestion in nasal administration, $cm^3$ (M±m, n=9). The onset time of the therapeutic effect provided by administration of Compound I was no more than 5 minutes, the duration of the therapeutic effect was at least 8 hours.

Thus, when administered intranasally, Compound I is a potent decongestant with a high onset time of the effect and a duration of action of at least 8 hours.

TABLE 4

| Group | Administration of the preparation | Before histamine administration | | Time after histamine administration, minutes | | | |
|---|---|---|---|---|---|---|---|
| | | | | 5 | | 10 | |
| | | Left nostril | Right nostril | Left nostril | Right nostril | Left nostril | Right nostril |
| Control | 5 minutes after histamine administration | 4.6 ± 0.1 | 4.5 ± 0.1 | 2.4 ± 0.1$ | 2.8 ± 0.2$ | 2.1 ± 0.2$ | 2.3 ± 0.2$ |
| Compound I (1% solution) | | 3.9 ± 0.4 | 3.8 ± 0.3 | 4.2 ± 0.4&$ | 4.8 ± 0.1&$ | 4.3 ± 0.2$ | 4.7 ± 0.2&$ |
| Control | Right before histamine administration | 4.1 ± 0.2 | 4.2 ± 0.1 | 2.7 ± 0.2$ | 2.5 ± 0.2$ | 2.0 ± 0.2$ | 2.0 ± 0.2$ |
| Compound I (1% solution) | | 3.6 ± 0.2 | 3.9 ± 0.5 | 3.2 ± 0.1& | 3.4 ± 0.1& | 2.8 ± 0.1&$ | 2.7 ± 0.1&$ |
| Control | 3 hours before histamine administration | 5.1 ± 0.3 | 5.2 ± 0.2 | 2.8 ± 0.3$ | 2.6 ± 0.3$ | 2.6 ± 0.4$ | 2.7 ± 0.4$ |
| Compound I (1% solution) | | 4.8 ± 0.2 | 4.9 ± 0.2 | 2.4 ± 0.3$ | 2.2 ± 0.3$ | 2.9 ± 0.3$ | 3.3 ± 0.4$ |
| Control | 6 hours before histamine administration | 4.5 ± 0.2 | 4.4 ± 0.2 | 2.9 ± 0.3$ | 2.8 ± 0.3$ | 2.5 ± 0.2$ | 2.4 ± 0.2$ |
| Compound I (1% solution) | | 4.5 ± 0.2 | 4.1 ± 0.2 | 3.6 ± 0.2& | 3.4 ± 0.2& | 3.8 ± 0.2&$ | 4 ± 0.3&$ |
| Control | 8 hours before histamine administration | 4.2 ± 0.1 | 4.3 ± 0.1 | 2.6 ± 0.1$ | 2.9 ± 0.2$ | 2.4 ± 0.2$ | 2.3 ± 0.1$ |
| Compound I (1% solution) | | 4.5 ± 0.1 | 4.1 ± 0.1 | 3.0 ± 0.2$ | 2.8 ± 0.2$ | 2.9 ± 0.1&$ | 2.8 ± 0.2&$ |

| Group | Administration of the preparation | Time after histamine administration, minutes | | | |
|---|---|---|---|---|---|
| | | 15 | | 20 | |
| | | Left nostril | Right nostril | Left nostril | Right nostril |
| Control | 5 minutes after histamine administration | 1.7 ± 0.1$ | 1.5 ± 0.1$ | 1.6 ± 0.2$ | 1.8 ± 0.1$ |
| Compound I (1% solution) | | 4.6 ± 0.5 | 4.6 ± 0.3& | 4.2 ± 0.2& | 4.6 ± 0.4 |
| Control | Right before histamine administration | 1.3 ± 0.1$ | 1.3 ± 0.1$ | 1.6 ± 0.1$ | 1.5 ± 0.1$ |
| Compound I (1% solution) | | 3.2 ± 0.3& | 3.4 ± 0.3& | 3.4 ± 0.2& | 3.3 ± 0.1& |
| Control | 3 hours before histamine administration | 1.6 ± 0.2$ | 1.8 ± 0.2$ | 1.2 ± 0.1$ | 1.3 ± 0.1$ |
| Compound I (1% solution) | | 2.7 ± 0.4&$ | 2.8 ± 0.4&$ | 2.2 ± 0.2&$ | 2.1 ± 0.2&$ |
| Control | 6 hours before histamine administration | 1.9 ± 0.3$ | 1.9 ± 0.2$ | 0.9 ± 0.2$ | 0.9 ± 0.2$ |
| Compound I (1% solution) | | 3.9 ± 0.5& | 3.5 ± 0.2&$ | 3.7 ± 0.1&$ | 3.6 ± 0.2&$ |
| Control | 8 hours before histamine administration | 1.4 ± 0.1$ | 1.2 ± 0.1$ | 0.8 ± 0.1$ | 0.9 ± 0.2$ |
| Compound I (1% solution) | | 2.0 ± 0.1&$ | 1.9 ± 0.2&$ | 1.7 ± 0.1&$ | 1.8 ± 0.2&$ |

| Group | Administration of the preparation | Time after histamine administration, minutes | | | |
|---|---|---|---|---|---|
| | | 30 | | 40 | |
| | | Left nostril | Right nostril | Left nostril | Right nostril |
| Control | 5 minutes after histamine administration | 2.5 ± 0.1$ | 2.2 ± 0.2$ | 3.4 ± 0.2$ | 3.5 ± 0.2$ |
| Compound I (1% solution) | | 4.6 ± 0.1& | 4.9 ± 0.2&$ | 4.5 ± 0.3& | 4.8 ± 0.4& |
| Control | Right before histamine administration | 2.1 ± 0.1$ | 2.4 ± 0.1$ | 3.4 ± 0.1$ | 3.4 ± 0.1$ |
| Compound I (1% solution) | | 3.1 ± 0.2& | 3.2 ± 0.0& | 4.1 ± 0.3 | 4.0 ± 0.1& |
| Control | 3 hours before histamine administration | 2.1 ± 0.3$ | 2.2 ± 0.2$ | 2.8 ± 0.3$ | 2.7 ± 0.4$ |
| Compound I (1% solution) | | 2.9 ± 0.2$ | 3.0 ± 0.1&$ | 3.6 ± 0.1&$ | 3.6 ± 0.1&$ |

TABLE 4-continued

| | | | | | |
|---|---|---|---|---|---|
| Control Compound I (1% solution) | 6 hours before histamine administration | 2.9 ± 0.1$ 4.3 ± 0.2& | 3.0 ± 0.1$ 3.8 ± 0.1&$ | 3.4 ± 0.2$ 3.3 ± 0.1$ | 3.5 ± 0.2$ 3.8 ± 0.2$ |
| Control Compound I (1% solution) | 8 hours before histamine administration | 1.9 ± 0.2$ 2.7 ± 0.2&$ | 2.0 ± 0.1$ 2.5 ± 0.2&$ | 3.5 ± 0.1$ 3.6 ± 0.2$ | 3.5 ± 0.1$ 3.5 ± 0.2$ |

| | | Time after histamine administration, minutes | | | |
|---|---|---|---|---|---|
| | | 50 | | 60 | |
| Group | Administration of the preparation | Left nostril | Right nostril | Left nostril | Right nostril |
| Control Compound I (1% solution) | 5 minutes after histamine administration | 3.3 ± 0.1$ 4.2 ± 0.2& | 3.6 ± 0.1$ 4.1 ± 0.4 | 3.5 ± 0.2$ 5.2 ± 0.5& | 3.3 ± 0.1$ 5.2 ± 0.3&$ |
| Control Compound I (1% solution) | Right before histamine administration | 3.5 ± 0.2$ 3.4 ± 0.4 | 3.9 ± 0.1 3.4 ± 0.1 | 3.4 ± 0.1$ 3.2 ± 0.2 | 3.8 ± 0.1$ 3.6 ± 0.3 |
| Control Compound I (1% solution) | 3 hours before histamine administration | 3.2 ± 0.2$ 2.8 ± 0.2$ | 3.3 ± 0.3 2.7 ± 0.2$ | 5.1 ± 0.3 5.0 ± 0.2 | 5.1 ± 0.1 5.2 ± 0.3 |
| Control Compound I (1% solution) | 6 hours before histamine administration | 3.5 ± 0.3$ 3.9 ± 0.1$ | 3.6 ± 0.3$ 4.2 ± 0.2 | 3.7 ± 0.3 4.0 ± 0.0 | 3.8 ± 0.3 4.5 ± 0.3$ |
| Control Compound I (1% solution) | 8 hours before histamine administration | 3.6 ± 0.1 3.7 ± 0.1 | 3.5 ± 0.1$ 3.7 ± 0.2 | 3.9 ± 0.2 4.1 ± 0.2 | 3.7 ± 0.2$ 4 ± 0.2$ |

Note:
*difference from the intact group by Student's t-test ($p<0.05$)
&difference from the control group by Student's t-test ($p<0.05$)

Example 8. Study of the Activity of Compound I in Oral Administration on a Histamine-Induced Nasal Congestion Model in Dogs A histamine-induced nasal congestion model in dogs was performed according to the standard procedure [Tiniakov R. L., Tiniakova O. P., McLeod R. L., Hey J. A., Yeates D. B. Canine model of nasal congestion and allergic rhinitis//J Appl Physiol. 2003. V.94(5). P.1821-1828]. Beagle dogs were injected in the nasal cavity with a 5% histamine solution in a volume of 250 μl/nostril. The volume of the nasal cavity of the right and left nostrils was measured using a rhinometer before and 5, 10, 15, 20, 30, 40, 50 and 60 minutes after administration of histamine. Three experiments were performed, in which Compound I was administered orally once at different times: 1) 30 minutes before administration of histamine; 2) 1 hour before administration of histamine; and 3) 6 hours before administration of histamine, and one experiment was performed, in which Compound I was administered orally once daily for 14 days, the last administration was carried out 1 hour before administration of histamine.

The results of the study showed that inhalation of the 5% histamine solution in dogs reduced the volume of the nasal cavity of the nostrils in animals. A single oral administration of Compound I provided a significant dose-dependent increase in the reduced volume of the nasal cavity of the nostrils in dogs. Compound I exerted a therapeutic effect when it was administered 30 minutes, 1 hour, and 6 hours before inhalation of histamine (Tables 5-7). Multiple daily administration of Compound I for 14 days also increased the reduced nasal cavity volume in dogs. The duration of administration of Compound I did not change the intensity of the therapeutic effect (Table 8).

Based on the resulting data it can be concluded that Compound I has a pronounced therapeutic effect of reducing nasal congestion. The onset of the therapeutic effect occurs within the first 30 minutes after a single administration of Compound I, the duration of the effect is at least 6 hours. Compound I reduces nasal congestion in both single and multiple use. Tolerance to Compound I is not generated.

TABLE 5

| | | Before histamine administration | | Time after histamine administration, minutes | | |
|---|---|---|---|---|---|---|
| | | | | 5 | | 10 |
| Group | Dose, mg/kg | Left nostril | Right nostril | Left nostril | Right nostril | Left nostril |
| Control | | 4.4 ± 0.2 | 4.4 ± 0.2 | 3.0 ± 0.2$ | 2.9 ± 0.2$ | 2.2 ± 0.2$ |
| Compound I (1% solution) | 0.005 | 4.3 ± 0.3 | 4.6 ± 0.3 | 3.5 ± 0.2$ | 3.4 ± 0.1$ | 2.6 ± 0.2$ |
| | 0.05 | 4.3 ± 0.2 | 4.2 ± 0.2 | 3.4 ± 0.1$ | 3.3 ± 0.2$ | 2.5 ± 0.1$ |
| | 0.54 | 4.5 ± 0.1 | 4.5 ± 0.3 | 2.9 ± 0.1$ | 3.0 ± 0.2$ | 2.6 ± 0.1$ |

TABLE 5-continued

| | | Time after histamine administration, minutes | | | | |
|---|---|---|---|---|---|---|
| | | 10 | 15 | | 20 | |
| Group | Dose, mg/kg | Right nostril | Left nostril | Right nostril | Left nostril | Right nostril |
| Control | | 2.0 ± 0.2$ | 1.9 ± 0.1$ | 1.8 ± 0.1$ | 1.5 ± 0.1$ | 1.5 ± 0.1$ |
| Compound I | 0.005 | 2.5 ± 0.2$ | 2.2 ± 0.2$ | 2.1 ± 0.2$ | 1.9 ± 0.3 | 2.0 ± 0.2$ |
| (1% solution) | 0.05 | 2.4 ± 0.2$ | 2.8 ± 0.1&$ | 2.6 ± 0.2&$ | 3.3 ± 0.1&$ | 3.3 ± 0.3&$ |
| | 0.54 | 2.5 ± 0.1$ | 3.7 ± 0.3&$ | 3.8 ± 0.1&$ | 3.8 ± 0.2& | 3.7 ± 0.1&$ |

| | | Time after histamine administration, minutes | | | |
|---|---|---|---|---|---|
| | | 30 | | 40 | |
| Group | Dose, mg/kg | Left nostril | Right nostril | Left nostril | Right nostril |
| Control | | 2.1 ± 0.1$ | 2.2 ± 0.2$ | 3.5 ± 0.1$ | 3.3 ± 0.1$ |
| Compound I | 0.005 | 2.5 ± 0.1&$ | 2.8 ± 0.2&$ | 3.9 ± 0.1& | 3.8 ± 0.2& |
| (1% solution) | 0.05 | 4.1 ± 0.1& | 3.8 ± 0.1& | 4.2 ± 0.3& | 4.2 ± 0.2& |
| | 0.54 | 3.8 ± 0.1&$ | 3.8 ± 0.2&$ | 4.2 ± 0.3& | 4.2 ± 0.3& |

| | | Time after histamine administration, minutes | | | |
|---|---|---|---|---|---|
| | | 50 | | 60 | |
| Group | Dose, mg/kg | Left nostril | Right nostril | Left nostril | Right nostril |
| Control | | 3.6 ± 0.1$ | 3.4 ± 0.2$ | 4.0 ± 0.1 | 3.9 ± 0.2 |
| Compound I | 0.005 | 3.9 ± 0.1& | 4.0 ± 0.2& | 4.0 ± 0.1 | 3.5 ± 0.1$ |
| (1% solution) | 0.05 | 4.2 ± 0.1& | 4.5 ± 0.1& | 4.3 ± 0.1 | 4.5 ± 0.3 |
| | 0.54 | 3.9 ± 0.2$ | 4.0 ± 0.3 | 4.0 ± 0.1$ | 4.2 ± 0.3 |

Note:
*difference from the baseline by Student's t-test ($p<0.05$)
&difference from the control group by Student's t-test ($p<0.05$)

TABLE 6

The volume of the nasal cavity of right and left nostrils in dogs on the experimental histamine-induced nasal congestion model in oral administration 1 hour before histamine administration, $cm^3$ (M ± m, n = 9)

| | | Before histamine administration | | Time after histamine administration, minutes | | |
|---|---|---|---|---|---|---|
| | | | | 5 | | 10 |
| Group | Dose, mg/kg | Left nostril | Right nostril | Left nostril | Right nostril | Left nostril |
| Control | | 4.2 ± 0.2 | 4.1 ± 0.1 | 3.4 ± 0.4 | 3.3 ± 0.1$ | 2.3 ± 0.2$ |
| Compound I | 0.005 | 3.9 ± 0.2 | 4.3 ± 0.2 | 3.1 ± 0.2$ | 3.1 ± 0.5$ | 2.4 ± 0.4$ |
| (1% solution) | 0.05 | 4.0 ± 0.3 | 4.2 ± 0.2 | 2.8 ± 0.1$ | 2.8 ± 0.3$ | 3.1 ± 0.24$ |
| | 0.54 | 4.1 ± 0.1 | 4.4 ± 0.1 | 2.6 ± 0.1$ | 3.0 ± 0.4$ | 3.4 ± 0.14$ |

| | | Time after histamine administration, minutes | | | | |
|---|---|---|---|---|---|---|
| | | 10 | 15 | | 20 | |
| Group | Dose, mg/kg | Right nostril | Left nostril | Right nostril | Left nostril | Right nostril |
| Control | | 2.2 ± 0.3$ | 1.9 ± 0.2$ | 1.6 ± 0.2$ | 1.6 ± 0.2$ | 1.4 ± 0.2$ |
| Compound I | 0.005 | 2.1 ± 0.1$ | 2.2 ± 0.2$ | 2.8 ± 0.5$ | 2.3 ± 0.14$ | 2.6 ± 0.4$ |
| (1% solution) | 0.05 | 3.5 ± 0.24$ | 3.1 ± 0.14$ | 2.6 ± 0.2$ | 2.5 ± 0.14$ | 2.5 ± 0.14$ |
| | 0.54 | 3.0 ± 0.24$ | 2.5 ± 0.2$ | 3.0 ± 0.24$ | 2.5 ± 0.24$ | 2.8 ± 0.34$ |

TABLE 6-continued

The volume of the nasal cavity of right and left nostrils in dogs on
the experimental histamine-induced nasal congestion model in oral administration
1 hour before histamine administration, cm$^3$ (M ± m, n = 9)

| | | Time after histamine administration, minutes | | | |
|---|---|---|---|---|---|
| | | 30 | | 40 | |
| Group | Dose, mg/kg | Left nostril | Right nostril | Left nostril | Right nostril |
| Control | | 2.4 ± 0.2$ | 2.5 ± 0.3$ | 3.0 ± 0.2$ | 3.0 ± 0.1$ |
| Compound I | 0.005 | 2.0 ± 0.2$ | 3.0 ± 0.5$ | 3.6 ± 0.2 | 3.4 ± 0.2$ |
| (1% solution) | 0.05 | 3.6 ± 0.2& | 3.5 ± 0.2& | 3.7 ± 0.3& | 3.7 ± 0.2& |
| | 0.54 | 3.8 ± 0.2& | 3.6 ± 0.2& | 3.6 ± 0.1& | 3.6 ± 0.2& |

| | | Time after histamine administration, minutes | | | |
|---|---|---|---|---|---|
| | | 50 | | 60 | |
| Group | Dose, mg/kg | Left nostril | Right nostril | Left nostril | Right nostril |
| Control | | 3.4 ± 0.2$ | 3.1 ± 0.2$ | 3.2 ± 0.1$ | 3.2 ± 0.2$ |
| Compound I | 0.005 | 3.3 ± 0.2$ | 3.7 ± 0.2& | 3.4 ± 0.1$ | 3.5 ± 0.2$ |
| (1% solution) | 0.05 | 3.2 ± 0.1$ | 3.2 ± 0.1$ | 3.2 ± 0.1$ | 3.5 ± 0.1$ |
| | 0.54 | 3.3 ± 0.3$ | 3.4 ± 0.1$ | 3.3 ± 0.2$ | 3.2 ± 0.2$ |

Note:
$difference from the baseline by Student's t-test (p<0.05)
&difference from the control group by Student's t-test (p<0.05)

TABLE 7

The volume of the nasal cavity of right and left nostrils in dogs on
the experimental histamine-induced nasal congestion model in oral administration
6 hours before histamine administration, cm$^3$ (M ± m, n = 9)

| | | Before histamine administration | | Time after histamine administration, minutes | | |
|---|---|---|---|---|---|---|
| | | | | 5 | | 10 |
| Group | Dose, mg/kg | Left nostril | Right nostril | Left nostril | Right nostril | Left nostril |
| Control | | 4.4 ± 0.1 | 4.5 ± 0.1 | 2.5 ± 0.1$ | 2.4 ± 0.2$ | 2.2 ± 0.2$ |
| Compound I | 0.005 | 4.4 ± 0.1 | 4.4 ± 0.2 | 2.0 ± 0.3$ | 2.1 ± 0.3$ | 1.9 ± 0.1$ |
| (1% solution) | 0.05 | 4.2 ± 0.2 | 4.1 ± 0.1 | 2.2 ± 0.1$ | 2.2 ± 0.2$ | 2.4 ± 0.2$ |
| | 0.54 | 4.1 ± 0.2 | 4.1 ± 0.2 | 2.7 ± 0.2$ | 2.7 ± 0.3$ | 2.8 ± 0.2& |

| | | Time after histamine administration, minutes | | | | |
|---|---|---|---|---|---|---|
| | | 10 | 15 | | 20 | |
| Group | Dose, mg/kg | Right nostril | Left nostril | Right nostril | Left nostril | Right nostril |
| Control | | 2.2 ± 0.1$ | 1.5 ± 0.1$ | 1.5 ± 0.1$ | 1.4 ± 0.1$ | 1.4 ± 0.1$ |
| Compound I | 0.005 | 2.0 ± 0.1$ | 2.4 ± 0.2& | 2.4 ± 0.1& | 3.2 ± 0.2& | 3.2 ± 0.2& |
| (1% solution) | 0.05 | 2.3 ± 0.2$ | 2.0 ± 0.2& | 2.0 ± 0.1& | 3.4 ± 0.1& | 3.2 ± 0.2& |
| | 0.54 | 2.8 ± 0.2& | 2.8 ± 0.1& | 2.8 ± 0.2& | 3.4 ± 0.1& | 3.5 ± 0.1& |

| | | Time after histamine administration, minutes | | | |
|---|---|---|---|---|---|
| | | 30 | | 40 | |
| Group | Dose, mg/kg | Left nostril | Right nostril | Left nostril | Right nostril |
| Control | | 2.0 ± 0.2$ | 2.0 ± 0.2$ | 3.2 ± 0.2$ | 3.2 ± 0.2$ |
| Compound I | 0.005 | 3.3 ± 0.1& | 3.4 ± 0.1& | 3.3 ± 0.2$ | 3.4 ± 0.1$ |
| (1% solution) | 0.05 | 3.4 ± 0.2& | 3.4 ± 0.1& | 3.1 ± 0.1$ | 3.1 ± 0.1$ |
| | 0.54 | 3.5 ± 0.2& | 3.4 ± 0.1& | 3.5 ± 0.1$ | 3.5 ± 0.1$ |

TABLE 7-continued

The volume of the nasal cavity of right and left nostrils in dogs on
the experimental histamine-induced nasal congestion model in oral administration
6 hours before histamine administration, cm$^3$ (M ± m, n = 9)

|  |  | Time after histamine administration, minutes | | | |
|---|---|---|---|---|---|
|  |  | 50 | | 60 | |
| Group | Dose, mg/kg | Left nostril | Right nostril | Left nostril | Right nostril |
| Control |  | 3.1 ± 0.1$ | 3.2 ± 0.1$ | 3.3 ± 0.1$ | 3.3 ± 0.1$ |
| Compound I | 0.005 | 3.4 ± 0.1$ | 3.5 ± 0.2$ | 3.6 ± 0.2$ | 3.4 ± 0.2$ |
| (1% solution) | 0.05 | 3.4 ± 0.1$ | 3.4 ± 0.1$ | 3.6 ± 0.1$ | 3.5 ± 0.1$ |
|  | 0.54 | 2.9 ± 0.1$ | 2.9 ± 0.2$ | 2.9 ± 0.1$ | 3.0 ± 0.1$ |

Note:
$difference from the baseline by Student's t-test (p<0.05)
&difference from the control group by Student's t-test (p<0.05)

TABLE 8

The volume of the nasal cavity of right and left nostrils in dogs on the experimental histamine-
induced nasal congestion model in oral administration for 14 days, cm$^3$ (M ± m, n = 9)

|  |  | Before histamine administration | | Time after histamine administration, minutes | | |
|---|---|---|---|---|---|---|
|  |  |  |  | 5 | | 10 |
| Group | Dose, mg/kg | Left nostril | Right nostril | Left nostril | Right nostril | Left nostril |
| Control |  | 4.4 ± 0.1 | 4.5 ± 0.2 | 2.7 ± 0.3$ | 2.7 ± 0.2$ | 2.5 ± 0.2$ |
| Compound I | 0.13 | 4.5 ± 0.1 | 4.5 ± 0.1 | 2.7 ± 0.2$ | 2.7 ± 0.2$ | 3.2 ± 0.2*$ |
| (1% solution) | 0.27 | 4.5 ± 0.2 | 4.5 ± 0.1 | 2.8 ± 0.2$ | 2.7 ± 0.2$ | 3.6 ± 0.2*$ |
|  | 0.54 | 4.4 ± 0.1 | 4.5 ± 0.1 | 3.1 ± 0.3$ | 2.7 ± 0.2$ | 3.4 ± 0.2*$ |

|  |  | Time after histamine administration, minutes | | | | |
|---|---|---|---|---|---|---|
|  |  | 10 | 15 | | 20 | |
| Group | Dose, mg/kg | Right nostril | Left nostril | Right nostril | Left nostril | Right nostril |
| Control |  | 2.6 ± 0.1$ | 1.7 ± 0.2$ | 1.7 ± 0.1$ | 1.5 ± 0.1$ | 1.5 ± 0.1$ |
| Compound I | 0.13 | 3.3 ± 0.2*$ | 2.5 ± 0.2*$ | 2.5 ± 0.1*$ | 2.4 ± 0.2*$ | 2.4 ± 0.2*$ |
| (1% solution) | 0.27 | 3.6 ± 0.2*$ | 2.8 ± 0.3*$ | 2.8 ± 0.2*$ | 2.7 ± 0.1*$ | 2.7 ± 0.2*$ |
|  | 0.54 | 3.4 ± 0.1*$ | 2.6 ± 0.1*$ | 2.6 ± 0.1*$ | 2.5 ± 0.2*$ | 2.5 ± 0.2*$ |

|  |  | Time after histamine administration, minutes | | | |
|---|---|---|---|---|---|
|  |  | 30 | | 40 | |
| Group | Dose, mg/kg | Left nostril | Right nostril | Left nostril | Right nostril |
| Control |  | 2.5 ± 0.2$ | 2.5 ± 0.2$ | 3.2 ± 0.1$ | 3.2 ± 0.1$ |
| Compound I | 0.13 | 3.2 ± 0.2*$ | 3.2 ± 0.2*$ | 3.6 ± 0.2*$ | 3.6 ± 0.2$ |
| (1% solution) | 0.27 | 3.3 ± 0.2*$ | 3.3 ± 0.1*$ | 3.8 ± 0.2*$ | 3.8 ± 0.2*$ |
|  | 0.54 | 3.5 ± 0.1*$ | 3.5 ± 0.2*$ | 3.7 ± 0.1*$ | 3.7 ± 0.2*$ |

|  |  | Time after histamine administration, minutes | | | |
|---|---|---|---|---|---|
|  |  | 50 | | 60 | |
| Group | Dose, mg/kg | Left nostril | Right nostril | Left nostril | Right nostril |
| Control |  | 3.5 ± 0.2$ | 3.4 ± 0.1$ | 3.6 ± 0.2$ | 3.6 ± 0.2$ |
| Compound I | 0.13 | 3.7 ± 0.2$ | 3.7 ± 0.2$ | 3.8 ± 0.1$ | 3.8 ± 0.1$ |
| (1% solution) | 0.27 | 3.7 ± 0.1$ | 3.7 ± 0.1$ | 3.8 ± 0.1$ | 3.8 ± 0.1$ |
|  | 0.54 | 3.7 ± 0.1$ | 3.7 ± 0.2$ | 3.8 ± 0.1$ | 3.8 ± 0.1$ |

Note:
$difference from the baseline by Student's t-test (p<0.05)
&difference from the control group by Student's t-test (p<0.05)

The invention claimed is:

1. A method of preventing and/or treating a disorder associated with activity of histamine receptor type 3 and/or 4 in a subject in need of such treatment, comprising administering a therapeutically effective amount of the compound 1:

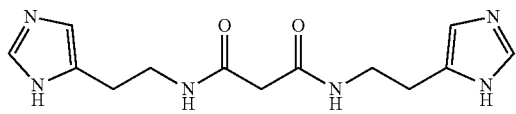 [SMILES: O=C(CC(=O)NCCc1cnc[nH]1)NCCc1cnc[nH]1]

or a pharmaceutically acceptable salt, hydrate or solvate thereof, to said subject.

2. A method of preventing and/or treating a disease selected from the group including itch, perennial or persistent allergic rhinitis in a subject in need of such treatment, comprising administering a therapeutically effective amount of a compound 1:

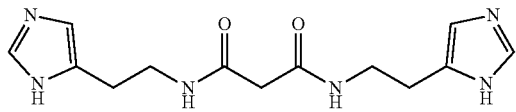 [SMILES: O=C(CC(=O)NCCc1cnc[nH]1)NCCc1cnc[nH]1]

or a pharmaceutically acceptable salt, hydrate or solvate thereof, to said subject.

3. A method for reducing the overactivation of histamine receptor type 3 and/or 4, comprising administering an effective amount of a compound 1:

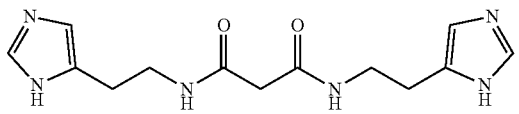 [SMILES: O=C(CC(=O)NCCc1cnc[nH]1)NCCc1cnc[nH]1]

or a pharmaceutically acceptable salt, hydrate or solvate thereof.

4. A method of treating a mammal, including a human, against a disorder that can be treated with antagonists of one or both of histamine receptor types 3 (H3) and (H4), including the simultaneous, separate or sequential administration of an effective amount of compound 1:

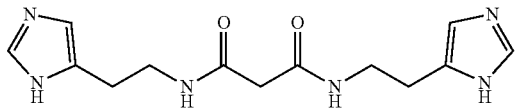

or a pharmaceutically acceptable salt, hydrate or solvate thereof.

* * * * *